(12) United States Patent
Hogan et al.

(10) Patent No.: US 12,253,491 B2
(45) Date of Patent: Mar. 18, 2025

(54) SYSTEMS AND METHODS FOR ANALYTE DETERMINATION

(71) Applicant: LA TROBE UNIVERSITY, Bundoora (AU)

(72) Inventors: Conor Hogan, Bundoora (AU); Darrell Elton, Bundoora (AU); Peter O'Conghaile, Bundoora (AU)

(73) Assignee: LA TROBE UNIVERSITY, Bundoora (AU)

( * ) Notice: Subject to any disclaimer, the term of this patent is extended or adjusted under 35 U.S.C. 154(b) by 640 days.

(21) Appl. No.: 17/595,394

(22) PCT Filed: May 15, 2020

(86) PCT No.: PCT/AU2020/050476
§ 371 (c)(1),
(2) Date: Nov. 16, 2021

(87) PCT Pub. No.: WO2020/227775
PCT Pub. Date: Nov. 19, 2020

(65) Prior Publication Data
US 2022/0229016 A1    Jul. 21, 2022

(30) Foreign Application Priority Data

May 16, 2019 (AU) .................. 2019901663

(51) Int. Cl.
*G01N 27/48* (2006.01)
*G01N 27/14* (2006.01)
(Continued)

(52) U.S. Cl.
CPC .......... *G01N 27/48* (2013.01); *G01N 27/308* (2013.01); *G01N 27/40* (2013.01); *G01N 27/413* (2013.01); *G01N 33/146* (2013.01)

(58) Field of Classification Search
CPC ...... G01N 27/48; G01N 27/308; G01N 27/40; G01N 27/413; G01N 33/146; G01N 33/0042
See application file for complete search history.

(56) References Cited

U.S. PATENT DOCUMENTS

2003/0155241 A1   8/2003  Lai et al.
2011/0171749 A1*  7/2011  Alocilja ............... B82Y 5/00
                                                  536/23.1
(Continued)

FOREIGN PATENT DOCUMENTS

CN    204536260 A    8/2015
CN    108802120 A    11/2018
(Continued)

OTHER PUBLICATIONS

Do Carmo et al., "Voltammetric Determination of Sulfite Using Graphite Paste Electrode Modified with Nanoparticles of Copper Pentacyanonitrosylferrate," ECS Transactions, 43 (1) 217-224 (2012) (Year: 2012).*
By Bakhsh et al., "Copper nanoparticles embedded chitosan for efficient detection and reduction of nitroaniline," International Journal of Biological Macromolecules, 131 (2019) 666-675 Available online Mar. 15, 2019 (Year: 2019).*
(Continued)

*Primary Examiner* — Alexander S Noguerola
(74) *Attorney, Agent, or Firm* — Vorys, Sater, Seymour and Pease LLP

(57) ABSTRACT

Described are systems and methods for the simple and rapid measurement of an analyte, such as sulphur dioxide, in liquid samples, including beverages such as wine or beer. The systems and methods utilize voltammetry with a particulate carbon or copper electrode, and may be conducted outside of a laboratory in ten to sixty seconds using a small portable instrument or mobile device using, for example, 2nd harmonic Fourier Transform (FT) AC voltammetry.

27 Claims, 12 Drawing Sheets

(a)

(b)

(51) Int. Cl.
    *G01N 27/30*     (2006.01)
    *G01N 27/40*     (2006.01)
    *G01N 27/413*    (2006.01)
    *G01N 33/14*     (2006.01)

(56) References Cited

U.S. PATENT DOCUMENTS

| | | |
|---|---|---|
| 2012/0132544 A1 | 5/2012 | Lawrence et al. |
| 2015/0027887 A1 | 1/2015 | Lee |
| 2017/0276634 A1 | 9/2017 | Saffell et al. |
| 2019/0072513 A1* | 3/2019 | Hogan ............... G10L 19/008 |
| 2019/0376930 A1 | 12/2019 | Arbault et al. |

FOREIGN PATENT DOCUMENTS

| | | |
|---|---|---|
| FR | 2892197 A1 | 4/2007 |
| JP | H09127053 A | 5/1997 |
| JP | 2008157930 A | 7/2008 |
| JP | 2012-177627 A | 9/2012 |
| WO | 2009031625 A1 | 3/2009 |
| WO | 2015060119 A1 | 4/2015 |
| WO | 2016/204635 A1 | 12/2016 |
| WO | 2017139352 A1 | 8/2017 |
| WO | 2018/154226 A1 | 8/2018 |
| WO | 2018/219991 A1 | 12/2018 |

OTHER PUBLICATIONS

Wikipedia photograph of the BASi epsilon C3 cell stand, 2004, downloaded Jun. 11, 2024 from https://bs.wikipedia.org/wiki/Datoteka:BASi_epsilon_C3_cell_stand.jpg (Year: 2004).*

Ipgi instruments photograph of the C3 Voltammetry Cell Stand, 2024, downloaded Jun. 11, 2024 from https://ipgi.co.in/basi-bipotentiostat-and-accessories/ (Year: 2024).*

Mayuri et al., "A bioinspired copper 2,2-bipyridyl complex immobilized MWCNT modified electrode prepared by a new strategy for elegant electrocatalytic reduction and sensing of hydrogen peroxide," Electrochimica Acta 240 (2017) 522-533 (Year: 2017).*

EPO computer generated English language translation of JP 2012177627 A, patent published Sep. 13, 2012 (Year: 2012).*

EPO computer generated English language translation of CN 108802120 A, patent published Nov. 13, 2018 (Year: 2018).*

Extended European Search Report (ESSR) issued in respect of corresponding European Patent Application 13844822.0 dated May 16, 2023.

Debbie S. Silvester: "Recent advances in the use of ionic liquids for electrochemical sensing", The Analyst, vol. 136, No. 23, Jan. 1, 2011, p. 4871.

An Office Action issued in respect of corresponding Chinese Patent Application No. 202080050749.0 dated Aug. 22, 2023 (English translation not provided).

* cited by examiner (a)

(b)

(a)

(b)

(a)

(b)

(a)

(b)

(a)

(b)

(a)

(b)

(a)

(b)

(a)

(b)

(a) (b)

SYSTEMS AND METHODS FOR ANALYTE DETERMINATION

FIELD

This disclosure relates to systems and methods for analyte determination, particularly, although not limited to, the voltammetric determination of analytes in foods and beverages. The systems and methods find application in, for example, the voltammetric determination of sulphur dioxide in wine.

BACKGROUND

The determination of sulphur dioxide in wine is one of the most important analytical problems in the food industry. Such analysis is required very frequently; a large winery may conduct thousands of sulphur dioxide analyses each year. However, current methods are either slow, expensive and accurate, or fast, cheap and inaccurate Sulphur dioxide is widely used in the food and drinks industries for its properties as a broad-spectrum preservative and antioxidant. In particular, the winemaking community has been using sulfur dioxide for the preservation of wine since antiquity. It is added to foods and beverages (usually in the form of a sulfite salt) to prevent undesirable microbial growth, discoloration and oxidative processes, to improve the quality and appearance of the products.

In aqueous media, sulphur dioxide exists in several forms: sulphite ($SO_3^{2-}$), bisulfite ($HSO_3^-$) and molecular sulphur dioxide ($SO_2$). These species exist in equilibrium with each other with the concentration of each defined by the pH, see equations 1 and 2.

$$SO_3^{2-} + H^+ \rightleftharpoons HSO_3^- \qquad (1)$$

$$HSO_3^- + H^+ \rightleftharpoons SO_2 + H_2O \qquad (2)$$

In wine, a proportion of these species may be bound to various other organic compounds in the beverage such as aldehydes or ketones. It is common to refer to the unbound sulphite, bisulfite and molecular sulphur dioxide collectively as "free sulphur dioxide"; whereas the bound species are referred to as "bound sulphur dioxide". The sum of these is then referred to as "total sulphur dioxide".

Sulphur dioxide is a known allergen, so total $SO_2$ is subject to strict regulation in most countries. Total $SO_2$ is typically measured at the bottling stage. Due to the complexity of the chemistry of $SO_2$ in wine, the concentration of free (i.e. unbound) $SO_2$ varies with time, and conditions. Therefore, it is beneficial to monitor the level of free $SO_2$ at each stage of wine production. Broadly speaking, free $SO_2$ is the important wine making parameter and total $SO_2$ is the value that is important with regards to legislative requirements.

Existing methods for $SO_2$ determination used in the wine industry (and other industries) are typically slow and cumbersome, requiring expensive instrumentations or elaborate methodologies; and considerable user expertise. As free $SO_2$ needs to be measured at many stages throughout the winemaking process, this is a particularly burdensome for winemakers and adds substantially to cost.

While methods that are fast and inexpensive do exist, such as colourimetric dip sticks, these are quite inaccurate and not widely used in the industry. Electrochemical methods of analysis based on voltammetry or amperometry in general, offer considerable advantages in terms of being adaptable into portable, easy to use, low-cost methodologies. The amperometric glucometer is perhaps the best-known example of this, where the instrumental hardware has been miniaturised into a simple hand-held potentiostatic device, and a printed disposable sensor is used in place of the permanent electrodes used in laboratory electroanalysis.

Voltammetric/amperometric methods of $SO_2$ determination have been studied by several authors [Compton et al Trends in Analytical Chemistry, Vol. 25, No. 6, 2006]; [Rodrigues et al J. Inst. Brew. 2017, 123: 45-48]. Most commonly, oxidation of sulphite to sulphate has been chosen as the basis for analysis and several methods have been reported. However, fouling of the electrode, leading to progressive loss in sensitivity and compromised reproducibility make this approach problematic. Also, selectivity problems arise due to the large over-potential required for sulphite oxidation.

On the other hand, detection of sulphur dioxide via electrochemical reduction has received comparatively little attention. This may seem surprising, as there are several advantages to cathodic rather than anodic detection; such as the avoidance of many oxidisable interferents. Also, by adjusting the pH, the equilibrium for equation 2 may be easily driven to the right to maximise the concentration of electro-reducible material. Furthermore, converting sulfite and bisulfite into $SO_2$ in this way may facilitate its separation from the sample matrix in the form of gas phase $SO_2$, allowing for the possibility of enhanced selectivity. The reduction of $SO_2$ under such acidic conditions (<pH 2), is believed to occur via a two electron two proton reaction as outlined in equation 3 [Compton et al J. Phys. Chem. B 2005, 109, 18500-18506].

$$SO_2 + 2e^- + 2H^+ \rightleftharpoons H_2SO_2 \qquad (3)$$

The main problem with cathodic detection, and the reason it has not been extensively used, is interference from cathodically active interferents, particularly dioxygen. $O_2$ undergoes reduction at a similar potential to sulfur dioxide and can therefore obscure the signal due to its reduction. Attempts have been made to counter this lack of selectivity by resorting to prior de-oxygenation or using elaborate means such as gas-diffusion micro-extraction or electrode modification with electron transfer mediators. Cardwell et al (Analyst, 1991, vol 116, 253) showed that it was possible to detect $SO_2$ in wine without the need for prior deoxygenation of the sample using 2nd harmonic AC voltammetry and a glassy carbon electrode. However, the method still suffered from interference from dioxygen and other species, it required elaborate, bespoke equipment which could not be readily miniaturised for use outside of a laboratory and each analysis took approximately ten minutes. Further, as the $SO_2$ signal decreased after each scan, the glassy carbon electrode required polishing of the active surface before each scan.

Apart from interference from dissolved dioxygen, another significant issue with detection of sulphur dioxide is interference from a class of compounds collectively referred to as polyphenols. Such compounds, which are frequently found in high concentration in red wine, often undergo reduction at a similar potential to sulphur dioxide and can therefore obscure the analytical signal of interest. These interfering compounds can be removed by the addition of so-called fining agents, prior to analysis. Suitable fining agents include proteins of animal origin, including casein, egg albumin, gelatin, and isinglass. However, this is an ineffective strategy because it disrupts the concentration of $SO_2$ in the sample and alters the balance of free and bound $SO_2$ in the sample in an unpredictable way.

None of these approaches may be regarded as satisfactory from the point of view of the need for a method which could be used for accurate, rapid analysis, outside of a laboratory environment by scientifically untrained personnel.

WO 2017/156584 discloses a method of voltammetric analysis of an analyte in a voltammetric cell using a mobile computing device, wherein the first channel of the audio signal output of the device is connected to the counter electrode of the voltammetric cell, the second channel of the audio signal output of the device is connected to the working electrode of the cell and the audio signal input of the device is connected to the working electrode of the cell. By applying an output voltage waveform comprising a time-varying voltammetric driving potential containing an AC perturbation between the first and second channels of the audio signal output, an input voltage waveform is received at the audio signal input which is recorded as a voltammetric response waveform.

In view of the foregoing there is a need for faster, more reliable and more broadly applicable systems and methods for analyte determination.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

The present disclosure relates to novel approaches to determining analyte concentrations. Described are systems and methods which allow simple and rapid measurement of an analyte, such as $SO_2$, in liquid samples, including beverages such as wine or beer. The systems and methods involve the use of voltammetry with, for example, a particulate carbon or copper electrode, and may be conducted outside of a laboratory in ten to sixty seconds using a small portable instrument or even a mobile device using, for example, 2nd harmonic Fourier Transform (FT) AC voltammetry.

The voltammetric sensing methodology significantly reduces the cost of sensing, and enables measurements to be made accurately, easily and quickly in the field, without the need to transport samples to a laboratory.

In a first aspect the present disclosure provides a system for detecting or measuring the concentration of an analyte via electrochemical reduction, said system comprising:
  (a) a source of time-variable voltammetric driving potential;
  (b) a working electrode, said working electrode having an active surface comprising one or both of particulate carbon and copper;
  (c) a counter electrode; and
  (d) means to measure a voltammetric response waveform;
wherein the working electrode and the counter electrode are connected to the source of time-variable voltammetric driving potential.

In some embodiments, the working electrode does not produce a voltammetric response due to the reduction of dioxygen which significantly overlaps with a voltammetric response due to the reduction of the analyte.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In a second aspect the present disclosure provides a system for detecting or measuring the concentration of an analyte via electrochemical reduction, said system comprising:
  (a) a source of time-variable voltammetric driving potential;
  (b) a working electrode, wherein the working electrode does not produce a voltammetric response due to the reduction of dioxygen which significantly overlaps with a voltammetric response due to the reduction of the analyte;
  (c) a counter electrode; and
  (d) means to measure a voltammetric response waveform;
    wherein the working electrode and the counter electrode are connected to the source of time-variable voltammetric driving potential.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In some embodiments, the working electrode has an active surface comprising one or both of particulate carbon and copper In some embodiments, the systems further comprises a voltammetric cell, said cell comprising a solution comprising the analyte.

In some embodiments of the presently disclosed systems, the working electrode and counter electrode are immersed in the solution comprising the analyte.

In other embodiments of the presently disclosed systems, the working electrode and counter electrode are not immersed in the solution comprising the analyte.

Preferably, when the working electrode comprises copper, the working electrode and counter electrode are not immersed in the solution comprising the analyte.

To address the problem of interference due to, for example, polyphenols, in the electrochemical analysis of, for example, $SO_2$ in red wine, advantageously, the electrodes, in some embodiments, are not immersed in the solution comprising the analyte.

In embodiments wherein the electrodes are not immersed in the analyte, the systems further comprises a membrane comprising electrolyte solution. In some embodiments, the membrane is saturated in electrolyte solution. The membrane comprising electrolyte solution is in contact with the electrodes.

In some embodiments, the electrodes and contacted membrane are located in the head-space above the solution comprising the analyte.

Advantageously, during operation of the systems, analyte is released from the solution into the head space and diffuses into the membrane comprising electrolyte solution enabling detection of the analyte. Such detection is free from interference from other potentially interfering components in the solution comprising the analyte, for example, free from interference from polyphenols in the case of red wine.

In a third aspect, the present disclosure provides a system for detecting or measuring the concentration of an analyte via electrochemical reduction, said system comprising:
  (a) a source of time-variable voltammetric driving potential;

(b) a working electrode, said working electrode having an active surface comprising one or both of particulate carbon and copper;
(c) a counter electrode;
(d) a voltammetric cell; and
(e) means to measure a voltammetric response waveform;

wherein the working electrode and the counter electrode are in contact with a membrane comprising electrolyte solution;

wherein the working electrode, counter electrode and contacted membrane are located in a head-space of the voltammetric cell; and wherein the working electrode and the counter electrode are connected to the source of time-variable voltammetric driving potential.

In some embodiments, the working electrode does not produce a voltammetric response due to the reduction of dioxygen which significantly overlaps with a voltammetric response due to the reduction of the analyte.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In a fourth aspect, the present disclosure provides a system for detecting or measuring the concentration of an analyte via electrochemical reduction, said system comprising:
(a) a source of time-variable voltammetric driving potential;
(b) a working electrode, wherein the working electrode does not produce a voltammetric response due to the reduction of dioxygen which significantly overlaps with a voltammetric response due to the reduction of the analyte;
(c) a counter electrode;
(d) a voltammetric cell; and
(e) means to measure a voltammetric response waveform;

wherein the working electrode and the counter electrode are in contact with a membrane comprising electrolyte solution;

wherein the working electrode, counter electrode and contacted membrane are located in a head-space of the voltammetric cell; and wherein the working electrode and the counter electrode are connected to the source of time-variable voltammetric driving potential.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In some embodiments, the working electrode has an active surface comprising one or both of particulate carbon and copper The membrane may be a thin membrane. The thickness of the membrane may be from about 0.01 micron to about 1000 micron, or from about 0.1 micron to about 500 micron, or from about 1 micron to about 200 micron, or from about 10 micron to about 100 micron.

The membrane may comprise any material which will retain a thin layer of liquid in intimate contact with the electrodes, while allowing gaseous analyte, for example $SO_2$, to diffuse into it. The membrane may be a hydrophilic material. The membrane may be microporous. Exemplary membranes include fine nylon mesh or paper.

In some embodiments, the source of time-variable voltammetric driving potential and the means to measure the voltammetric response waveform comprise a potentiostat.

In other embodiments, the source of time-variable voltammetric driving potential and the means to measure the voltammetric response waveform comprise a mobile computing device, such as a mobile phone.

In some embodiments, the working electrode and the counter electrode are wirelessly connected to the source of time-variable voltammetric driving potential.

In a fifth aspect the present disclosure provides a method for detecting or measuring the concentration of an analyte via electrochemical reduction, said method comprising:
(a) introducing into a solution comprising the analyte a working electrode and a counter electrode, said working electrode having an active surface comprising one or both of particulate carbon and copper;
(b) applying a time-variable voltammetric driving potential between the working and counter electrodes; and
(c) measuring the resulting voltammetric response waveform.

A preferred working electrode comprises particulate carbon.

In some embodiments, the working electrode does not produce a voltammetric response due to the reduction of dioxygen which significantly overlaps with a voltammetric response due to the reduction of the analyte.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In a sixth aspect the present disclosure provides a method for detecting or measuring the concentration of an analyte via electrochemical reduction, said method comprising:
(a) introducing into a solution comprising the analyte a working electrode and a counter electrode, wherein the working electrode does not produce a voltammetric response due to the reduction of dioxygen which significantly overlaps with a voltammetric response due to the reduction of the analyte;
(b) applying a time-variable voltammetric driving potential between the working and counter electrodes; and
(c) measuring the resulting voltammetric response waveform.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In some embodiments, the working electrode has an active surface comprising one or both of particulate carbon and copper. A preferred working electrode in such immersed mode of operation is particulate carbon.

In a seventh aspect the present disclosure provides a method for detecting or measuring the concentration of an analyte via electrochemical reduction, said method comprising:
(a) introducing into a head-space adjacent to a solution comprising the analyte a working electrode and a counter electrode, said working electrode having an active surface comprising one or both of particulate carbon and copper, said working electrode and counter electrode being in contact with a membrane, said membrane comprising electrolyte solution;

(b) applying a time-variable voltammetric driving potential between the working and counter electrodes; and (c) measuring the resulting voltammetric response waveform.

In some embodiments, the working electrode does not produce a voltammetric response due to the reduction of dioxygen which significantly overlaps with a voltammetric response due to the reduction of the analyte.

In some embodiments, the magnitude of the voltammetric response due to the reduction of dioxygen, at the potential of the peak voltammetric response due to reduction of the analyte, is less than 20%, or less than 10%, or less than 5%, or less than 2%, or less than 1% of the response due to reduction of the analyte, when said analyte is present at a concentration of 5 ppm.

In an eighth aspect the present disclosure provides a method for detecting or measuring the concentration of an analyte via electrochemical reduction, said method comprising:

(a) introducing into a head-space adjacent to a solution comprising the analyte a working electrode and a counter electrode, wherein the working electrode does not produce a voltammetric response due to the reduction of dioxygen which significantly overlaps with a voltammetric response due to reduction of the analyte, said working electrode and counter electrode being in contact with a membrane, said membrane comprising electrolyte solution;

(b) applying a time-variable voltammetric driving potential between the working and counter electrodes; and (c) measuring the resulting voltammetric response waveform.

In some embodiments, the magnitude of the voltammetric response due to the reduction of dioxygen, at the potential of the peak voltammetric response due to the reduction of the analyte, is less than 20%, or less than 10%, or less than 5%, or less than 2%, or less than 1% of the response due to reduction of the analyte, when said analyte is present at a concentration of 5 ppm.

In some embodiments the working electrode has an active surface comprising one or both of particulate carbon and copper In some embodiments, the membrane is saturated in electrolyte solution.

In some embodiments, the electrodes and contacted membrane are located in the head space above the solution comprising the analyte.

Advantageously, in performing the methods, analyte is released from the solution into the head space and diffuses into the membrane comprising electrolyte solution enabling detection of the analyte. Such detection is free from interference from other potentially interfering components in the solution comprising the analyte, for example, free from interference from polyphenols in the case of red wine.

The membrane may be a thin membrane. The thickness of the membrane may be from about 0.01 micron to about 1000 micron, or from about 0.1 micron to about 500 micron, or from about 1 micron to about 200 micron, or from about 10 micron to about 100 micron.

The membrane may comprise any material which will retain a thin layer of liquid in intimate contact with the electrodes, while allowing gaseous analyte, for example $SO_2$, to diffuse into it. The membrane may be a hydrophilic material. The membrane may be microporous. Exemplary membranes include fine nylon mesh or paper.

When the methods employ a copper working electrode it is advantageous to utilise the non-immersed (head-space) mode of operation. While not wishing to be bound by theory, it is believed that ions, such as chloride, if present in the solution comprising the analyte, may interfere with the copper working electrode when utilised in immersed mode. In non-immersed mode, such interference does not occur.

A further advantage of a copper working electrode is that, as $SO_2$ electrochemistry is reversible at a copper electrode in acidic media, it leads to an enhanced signal when AC voltammetric or pulsed DC voltammetric techniques are utilised. Furthermore, as dioxygen reduction is irreversible, enhanced discrimination against dioxygen is possible using AC voltammetric or pulsed DC voltammetric technique.

In some embodiments of the herein disclosed systems and methods, the working electrode does not substantially electrochemically reduce dioxygen at a potential between about 0 and about −1.0 volts.

In some embodiments, the application of the time-variable voltammetric driving potential and the measurement of the voltammetric response waveform comprise a potentiostat.

In other embodiments, the application of the time-variable voltammetric driving potential and the measurement of the voltammetric response waveform comprise a mobile computing device, such as a mobile phone.

In some embodiments, the application of the time-variable voltammetric driving potential and the measurement of the voltammetric response waveform are performed wirelessly.

In any one or more of the above disclosed aspects the working electrode may be an electrode coated in particulate carbon. The particulate carbon may be graphene or graphene like material. The electrode may be coated in graphene or graphene-like material. Alternatively, the working electrode may be a screen printed particulate carbon electrode. Other suitable particulate carbon electrodes include carbon paste electrodes or porous carbon electrodes. The particulate carbon electrode may also have a composite structure, for example, composites of particulate carbon with polymers, such as epoxy resin, silicone or PTFE.

In any one or more of the above disclosed aspects, the working electrode may be a copper electrode or an electrode comprising both particulate carbon and copper.

A particular advantage of the present systems and methods is that the signal due to background dioxygen is strongly diminished and often eliminated entirely. This allows analyte detection limits to be very low and obviates the need to deoxygenate samples. A further advantage is that the working electrode does not require polishing between voltammetric scans. It is envisaged that the herein disclosed systems and methods would find application in the determination of analytes such as hydrogen peroxide and certain metal ions, whose reduction potential is similar to that of dioxygen and whose electrochemical detection and/or quantification may be prejudiced by the presence of dioxygen.

The time-variable voltammetric driving potential may be selected from, for example, a DC ramp, for example, linear scan voltammetry or cyclic voltammetry, a series of square wave pulses superimposed on a DC ramp, for example, square wave voltammetry, or an AC waveform superimposed on a DC ramp, for example, AC voltammetry.

When a mobile device is utilized the time-variable voltammetric driving potential is selected from a series of square wave pulses superimposed on a DC ramp, for example, square wave voltammetry, or an AC waveform superimposed on a DC ramp, for example, AC voltammetry.

The systems or methods may further comprise a reference electrode.

The voltammetric analysis may be performed in two-electrode or three-electrode mode. The ability to use two-electrode mode allows the use of relatively simple potentiostatic instrumentation.

In some embodiments, the solution comprising the analyte has a pH between about 0.5 and about 5, preferably between about 0.6 and about 4, more preferably between about 0.6 and about 3, most preferably between about 0.6 and about 2.

In some embodiments, the reduction potential of the analyte is between about +0.2 volts and about −0.7 volts.

In some embodiments, the solution comprising the analyte comprises less than about 100 ppm dioxygen, or less than about 50 ppm, or less than about 30 ppm, or less than about 20 ppm, or less than about 10 ppm, or less than about 5 ppm.

In some embodiments, the solution comprising the analyte comprises between about 0.5 and about 100 ppm dioxygen, or between about 0.5 ppm and about 50 ppm dioxygen, or between about 0.5 ppm and about 30 ppm dioxygen, or between about 0.5 ppm and about 20 ppm dioxygen, or between about 0.5 ppm and about 10 ppm dioxygen, or between about 0.5 ppm and about 5 ppm dioxygen.

In some embodiments, the analyte comprises sulphur dioxide. The sulphur dioxide may be in the form a free sulphur dioxide and/or bound sulphur dioxide. The sum of free and bound sulphur dioxide is the total sulphur dioxide.

In some embodiments, the solution of the sample may be chemically pre-treated to release bound sulphur dioxide. For example, through treatment with a base such as sodium hydroxide. Such treatment enables analysis for total sulphur dioxide using the herein disclosed systems and methods.

In some embodiments, the total sulphur dioxide is present in an amount between about 1 ppm and about 400 ppm.

In some embodiments, the free sulphur dioxide is present in an amount between about 1 ppm and about 150 ppm.

In some embodiments, the dioxygen is present in an amount between about 0.5 ppm and about 50 ppm and the free sulphur dioxide is present in an amount between about 1 ppm and about 100 ppm, or between about 1 ppm and about 50 ppm.

In some embodiments, the solution comprising the analyte comprises a liquid food product.

In some embodiments, the liquid food product is a beverage.

In some embodiments, the beverage is selected from the group consisting of wine or beer.

In some embodiments, the wine has a polyphenol content from about 0.1 g/L to about 4 g/L.

In one embodiment, the presently disclosed method may be performed by bringing a sensor comprising a working electrode comprising one or both of particulate carbon or copper into contact with a solution of an analyte which has a pH between about 0.5 and about 2.0.

In another embodiment, the presently disclosed method may be performed by locating a sensor comprising a working electrode comprising one or both of particulate carbon or copper and a membrane comprising electrolyte solution contacted with the electrodes, in the head-space of a solution of an analyte which has a pH between about 0.5 and about 2.0.

In some embodiments, the frequency of the AC or square wave pulse component may be set to any suitable value, for example between about 10 Hz and about 200 Hz.

In some embodiments, the amplitude of the AC or square wave pulse component may be between about 5 and about 400 mV.

In some embodiments, the DC scan rate of the ramp may be of the order of about 100 mV/s.

In some embodiments, the potential may be scanned from any value between more positive than about −0.3 V to about −1.0 V.

In other embodiments, the herein disclosed systems and methods may be employed to measure atmospheric sulphur dioxide. In an example, a known volume of air may be bubbled through an alkaline solution and the solution then acidified and the sulphur dioxide measured as herein disclosed.

Further features and advantages of the present disclosure will be understood by reference to the following drawings and detailed description.

DETAILED DESCRIPTION OF THE EMBODIMENTS

Figure 1:
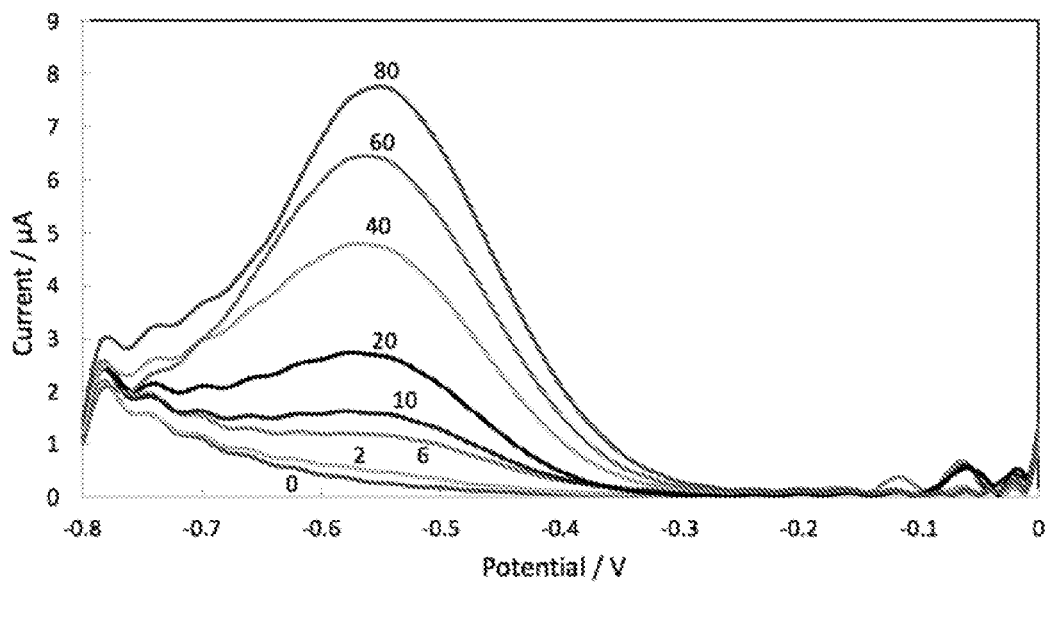
FIG. 1(a) is a plot of the voltammetric responses of solutions containing various concentrations of sulphur dioxide obtained using a conventional potentiostat.
FIG. 1(b) is a plot of the voltammetric responses of solutions containing various concentrations of sulphur dioxide obtained using a mobile phone.
Figure 1:
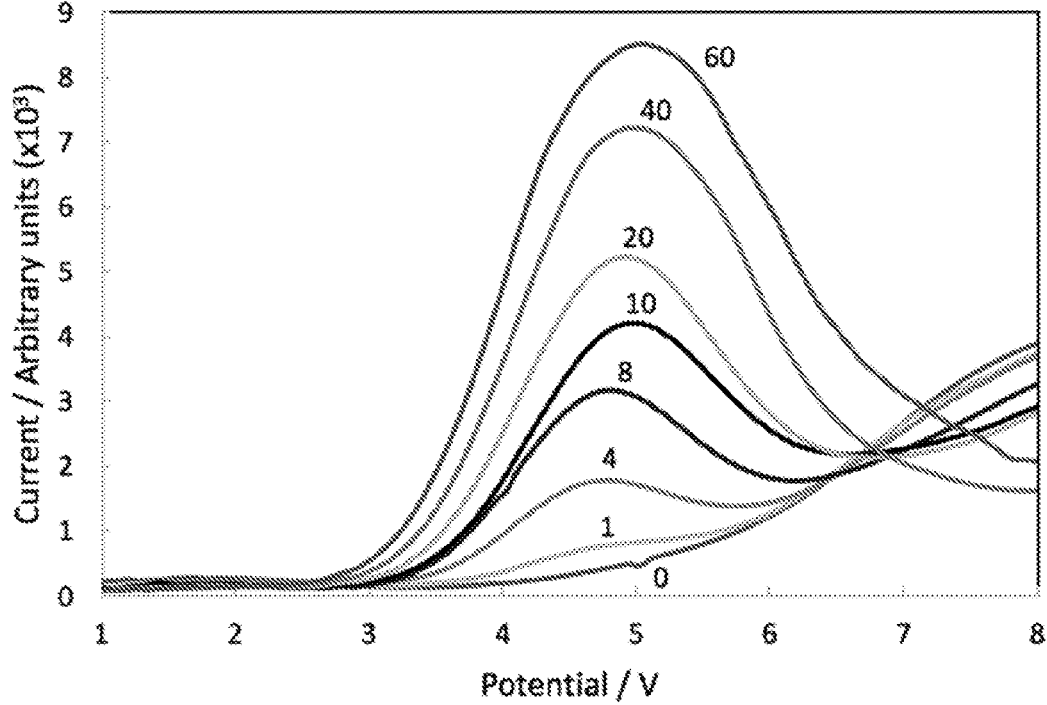

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any systems, devices, methods and materials similar or equivalent to those described herein can also be used in the practice or testing of the present disclosure, the preferred systems, devices, methods and materials are now described.

It must also be noted that, as used in the specification and the appended claims, the singular forms 'a', 'an' and 'the' include plural referents unless otherwise specified. Thus, for example, reference to 'analyte' may include more than one analyte, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless specifically stated or obvious from context, as used herein, the term 'about' is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any methods provided herein can be combined with one or more of any of the other methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

All potentials referred to herein are expressed relative to a standard Ag/AgCl electrode.

Reference will now be made in detail to exemplary embodiments of the disclosure. It is understood that the detailed examples and embodiments described herein are given by way of example for illustrative purposes only, and are in no way considered to be limiting to the disclosure.

In one illustrative embodiment, the presently disclosed methods may be performed by bringing a printed sensor, said sensor comprising at least a particulate carbon working electrode and a counter electrode, into contact with a solution of an analyte which has a pH of about 1.8. This may be effected using 0.2M KCl/HCl or other acid/electrolyte solution. An excitation voltage signal is then applied to the working electrode, comprising a DC ramp (i.e., cyclic voltammetry or linear scan voltammetry), or a series of square wave pulses superimposed on a DC ramp (i.e., square wave voltammetry); or an AC waveform superimposed on a DC ramp (i.e., AC voltammetry). The sensor may be disposable and/or mass produced.

The resulting current is monitored as a function of time and the data processed in the usual way for a voltammetric signal. For the FTAC method, this involves using a Fourier Transform (FT) to convert the current-time data into a power spectrum. Then, the frequency region of interest (usually corresponding to the $2^{nd}$ harmonic) is isolated and an inverse Fourier transform (IFT) is carried out on this data. An advantage of using higher harmonics in voltammetric analysis is that the higher harmonic responses are relatively free from non-Faradaic current components resulting in an improved signal to background ratio.

The analysis can be carried out using square wave voltammetry, conventional cyclic/linear scan voltammetry or amperometry if a potentiostat is used. However, the AC or pulsed method is required if a mobile device is used in place of a potentiostat, as taught in WO 2017/156584.

FIG. 1(a) shows typical results for the variation in $2^{nd}$ harmonic AC voltammetric signal with $SO_2$ concentration between 2 ppm and 80 ppm, including a 0 ppm blank run. $SO_2$ was added as sodium metabisulfite. The experiments were carried out using a standard potentiostat. FIG. 1(b) shows the results of a similar set of experiments to those shown in FIG. 1(a), except that the experiments were carried out using a mobile phone instead of a potentiostat. The added $SO_2$ concentration was between 1 and 60 ppm.

Figure 2:
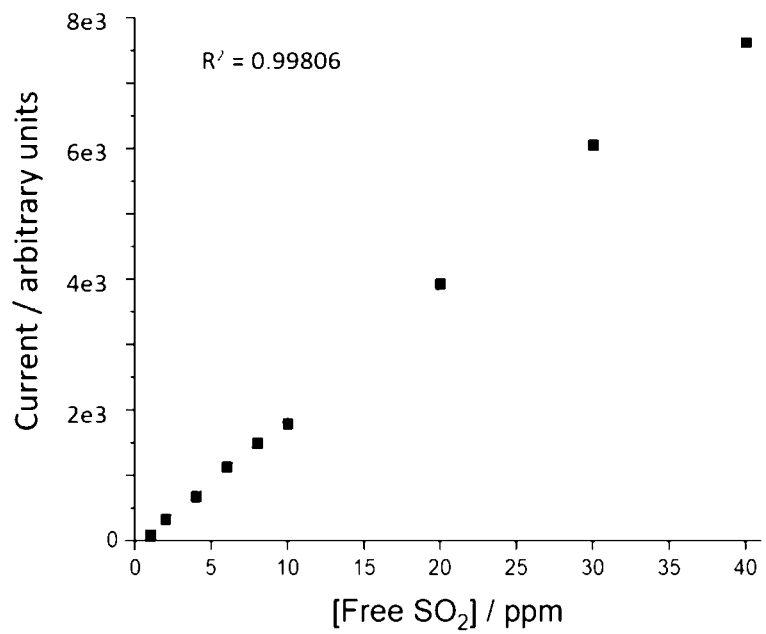
FIG. 2(a) shows the calibration curve for different concentrations of sulphur dioxide in pH 1.8 KCl/HCl solution, obtained using a mobile phone.
FIG. 2(b) shows the calibration curve for different concentrations of sulphur dioxide in pH 1.8 KCl/HCl solution, obtained using a potentiostat.
Figure 2:
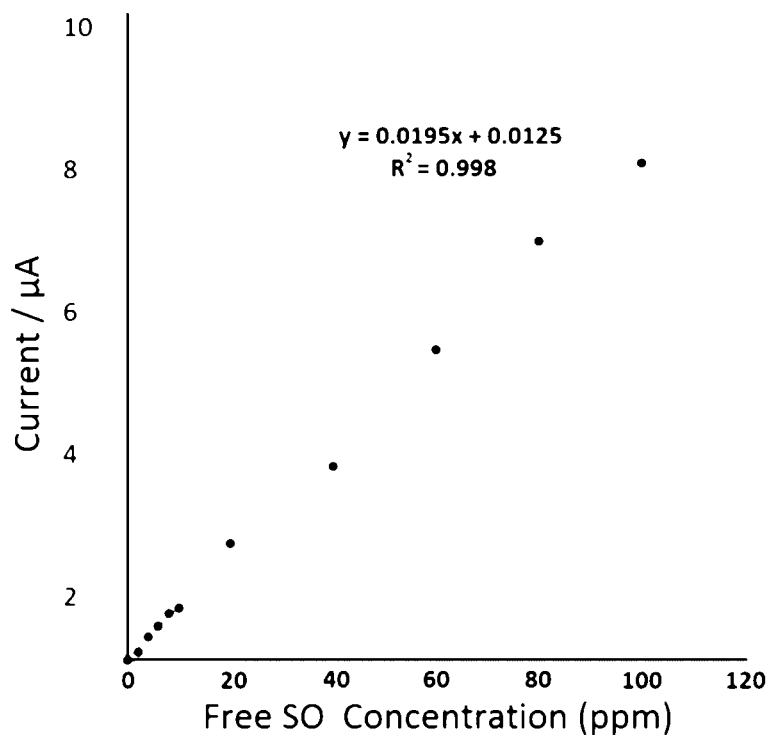

FIGS. 2(a) and 2(b) illustrate the calibration curves resulting from the analyses of FIG. 1. In both cases an excellent linear relationship results.

Figure 3:
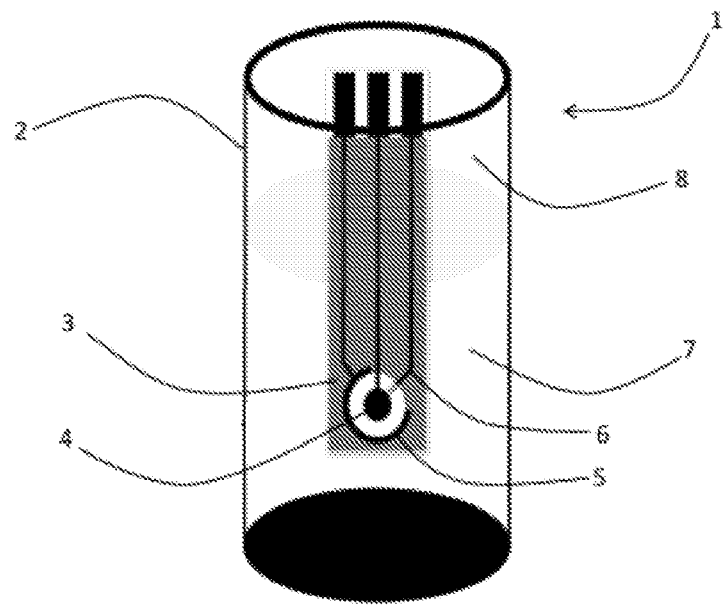
FIGS. 3(a) and 3(b) are schematic drawings of two modes of measurement according to embodiments of the present disclosure.
Figure 3:
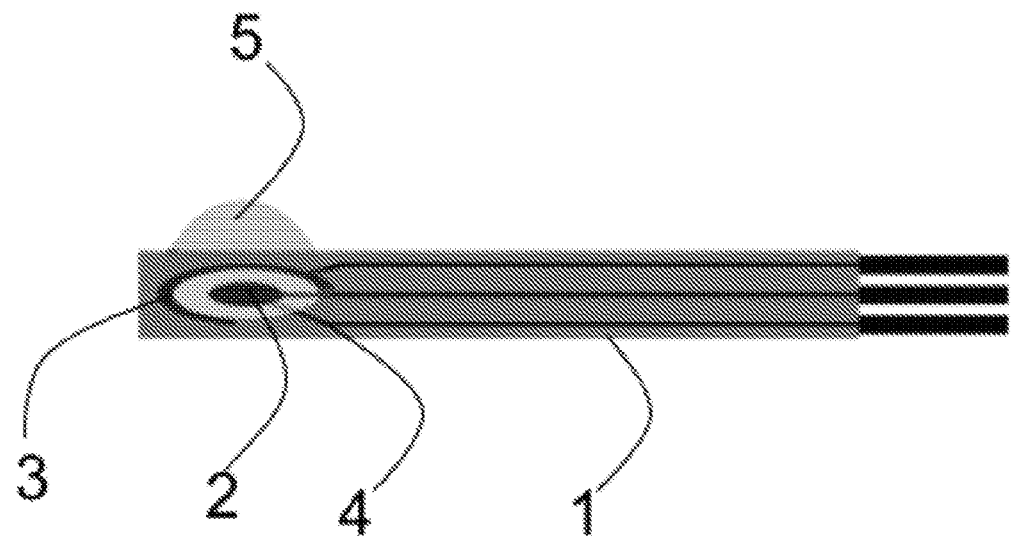

FIG. 3(a) illustrates part of a system according to one embodiment of the present disclosure including voltammetric cell (2) and electrode (3). The electrode is a three electrode assembly comprising working electrode (4), counter electrode (5) and reference electrode (6). The electrodes are immersed in a solution of analyte (7). Head space (8) above the solution of the analyte is also illustrated.

FIG. 3(b) illustrates that a drop of the analyte solution (5) may be placed on the sensor of the electrode assembly, including working electrode (2), counter electrode (3) and reference electrode (4). The advantage of this is that only a very small volume of sample is required. However, immersion of the sensor produces more reproducible results compared with the drop mode, because loss of volatile $SO_2$ from the sample is more rapid from the exposed sample droplet.

Figure 4:
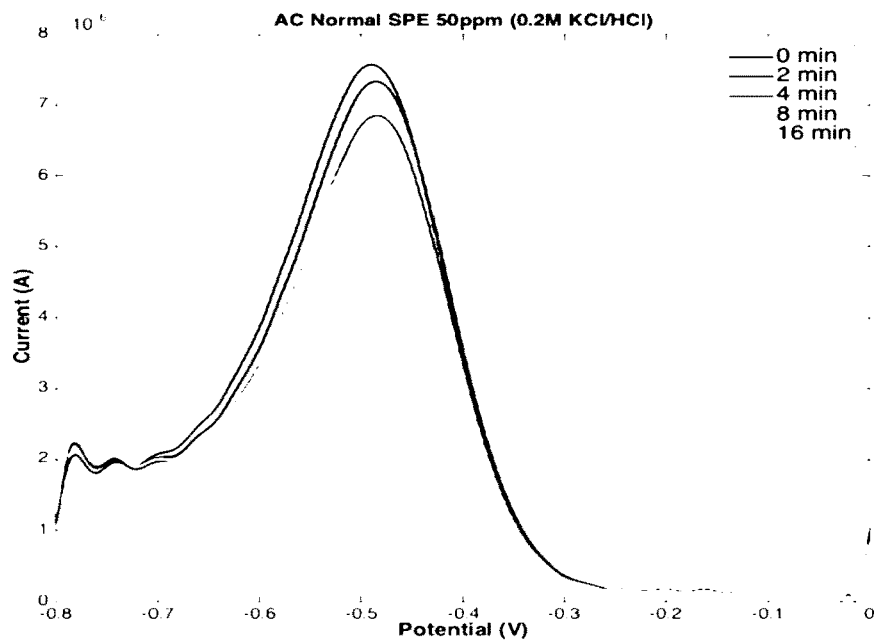
FIG. 4 are plots of the voltammetric responses over time for (a) electrodes immersed in solution and (b) a droplet of solution placed on electrodes.
Figure 4:
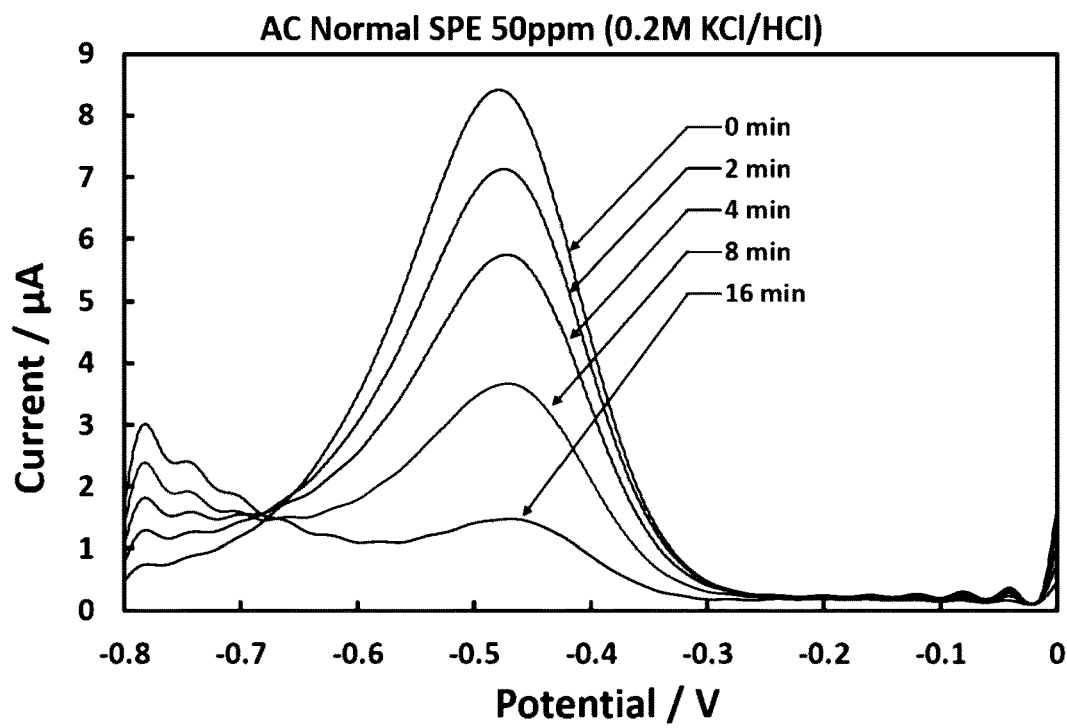

FIG. 4 illustrates this effect. FIG. 4(a) illustrates voltammograms measured periodically over a period of 16 minutes using the immersion method. FIG. 4(a) shows voltammograms measured at 0, 2, 4, 8 and 16 minutes and over time the voltammetric response does not substantially reduce over time. Reproducibility may be further improved if the measurement is made in a sealed sample vial. In contrast, FIG. 4(b) illustrates voltammograms measured periodically over a period of 16 minutes using a drop of analyte on a sensor. Voltammograms measured at 0, 2, 4, 8 and 16 minutes illustrate that the voltammetric response quickly falls over time.

Instead of acidifying the solution of the analyte it is also possible to immobilise an acid at the working electrode, thus simplifying the operation.

Discrimination against background dioxygen is key to reductive determination of $SO_2$. Surprisingly, when a working electrode composed of carbon particles is used, either in immersed or non-immersed mode, the signal due to background dioxygen is strongly diminished and often eliminated entirely. The carbon particles may be embedded in nonconductive organic binder, for example epoxy, silicone or PTFE.

In some embodiments, the working electrode is preferably a printed sensor with the working electrode comprising particulate carbon which effectively discriminates against background dioxygen.

In some embodiments, particularly in non-immersed mode, the working electrode is preferably a printed sensor with the working electrode comprising particulate carbon or copper or a mixture of particulate carbon and copper which effectively discriminates against background interferences.

Figure 5:
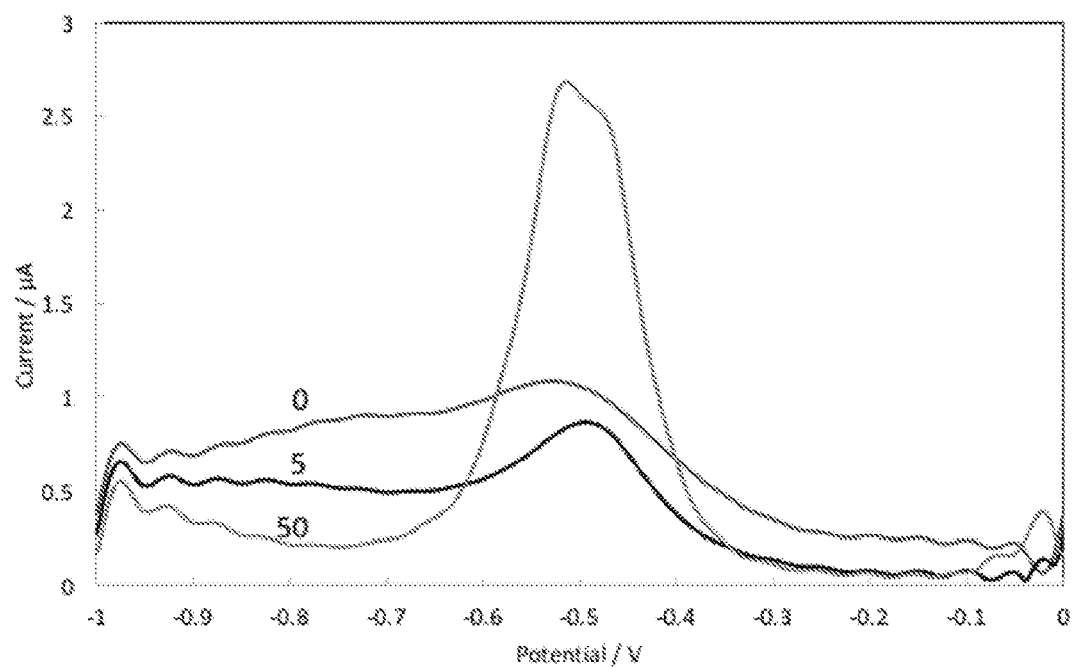
FIG. 5(a) shows the $2^{nd}$ harmonic FTAC response using a glassy carbon electrode for different concentrations of sulphur dioxide and FIG. 5(b) shows a SEM of the electrode surface.
Figure 5:
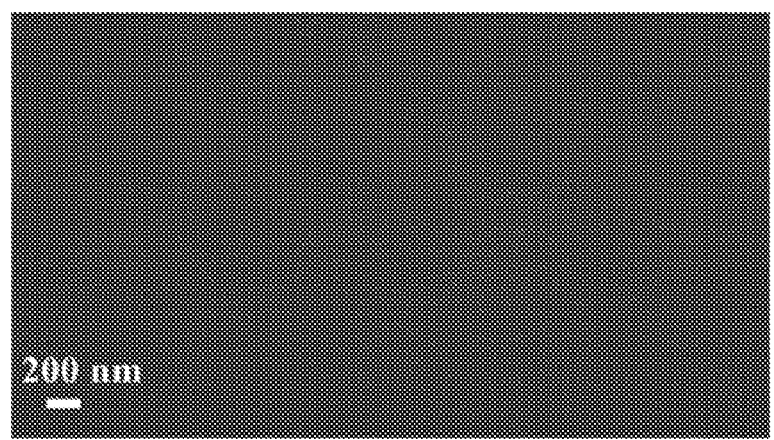

FIG. 5(a) illustrates the $2^{nd}$ harmonic FTAC voltammetric responses at $SO_2$ levels of 0 ppm, 5 ppm and 50 ppm for a conventional working electrode material (glassy carbon). The blank (0 ppm) shows a distinctive peak due to dioxygen reduction at approximately −0.4V. As this peak coincides with the reduction peak for $SO_2$, the 5 ppm $SO_2$ standard is not detectable. This constrains the limit of detection to approximately 10 ppm and the quantification limit to about 20 ppm. FIG. 5(b) shows a scanning electron micrograph (SEM) of the essentially featureless surface of the glassy carbon electrode.

Figure 6:
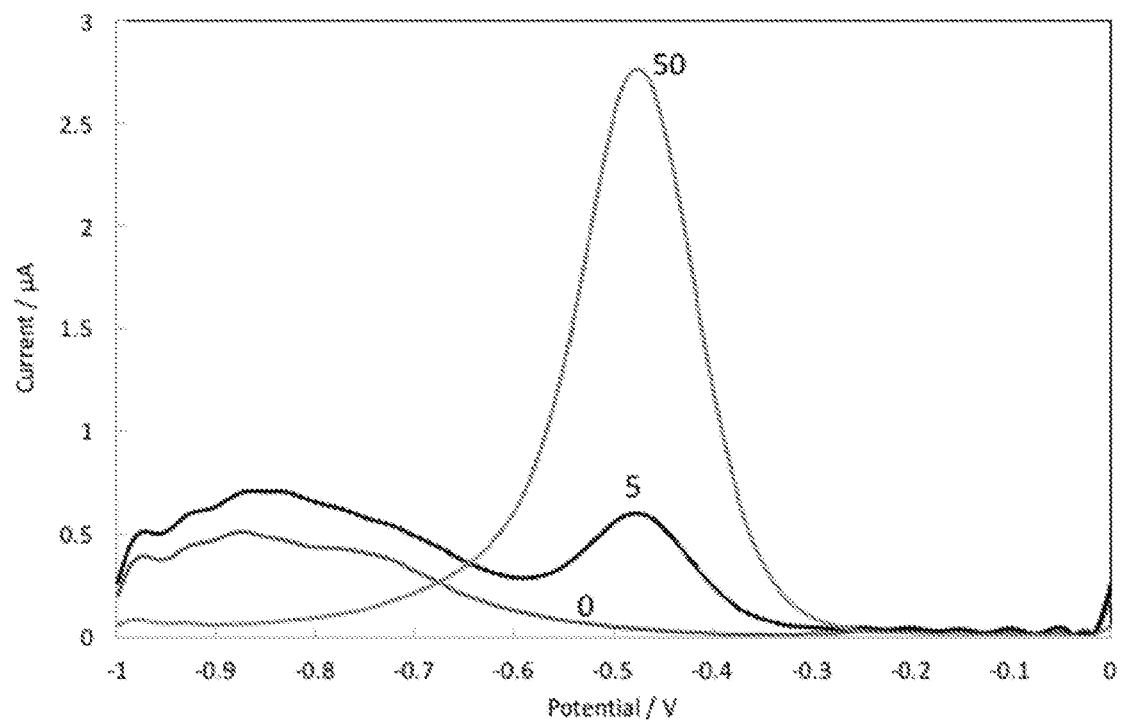
FIG. 6(a) shows the $2^{nd}$ harmonic FTAC response using a particulate carbon electrode for different concentrations of sulphur dioxide and FIG. 6(b) shows a SEM of the electrode surface.
Figure 6:
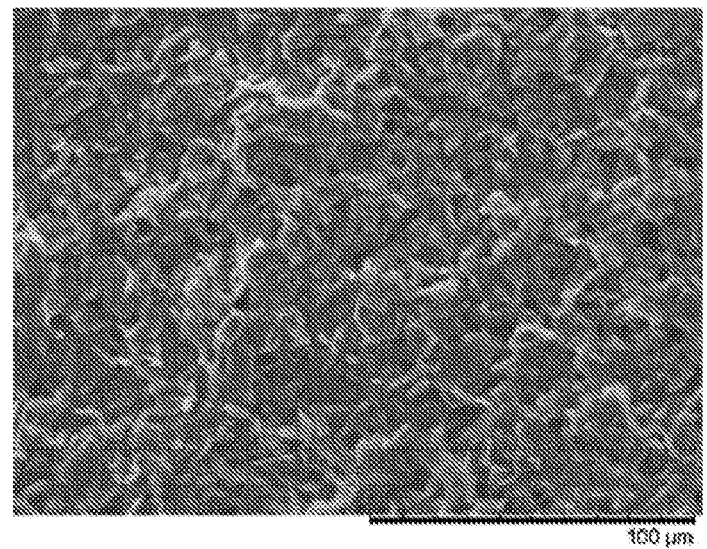

In contrast, FIG. 6(a) illustrates the $2^{nd}$ harmonic FTAC voltammetric responses at $SO_2$ levels of 0 ppm, 5 ppm and 50 ppm for a screen printed particulate carbon electrode. The blank (0 ppm) shows no peak due to dioxygen reduction, allowing $SO_2$ to be detected to levels below 1 ppm and the limit of quantification to approximately 2 ppm. FIG. 6(b) shows a SEM of particulate carbon electrode surface.

The printed particulate carbon electrode used for the experiments was a commercially available screen printed electrode manufactured by Zensor R&D Co., Ltd.

Similar results were obtained using screen printed particulate carbon electrodes purchased from Pine Research Instrumentation and also graphene coated electrodes. It is envisaged that any particulate carbon electrode will offer similar advantages.

Working electrodes comprised of other carbon materials such as mesoporous carbon or carbon nanotubes gave a large reduction peak for dioxygen and were therefore not capable of detecting low concentrations of $SO_2$. Similarly, platinum electrodes and gold electrodes give a large signal due to dioxygen reduction.

Figure 7:
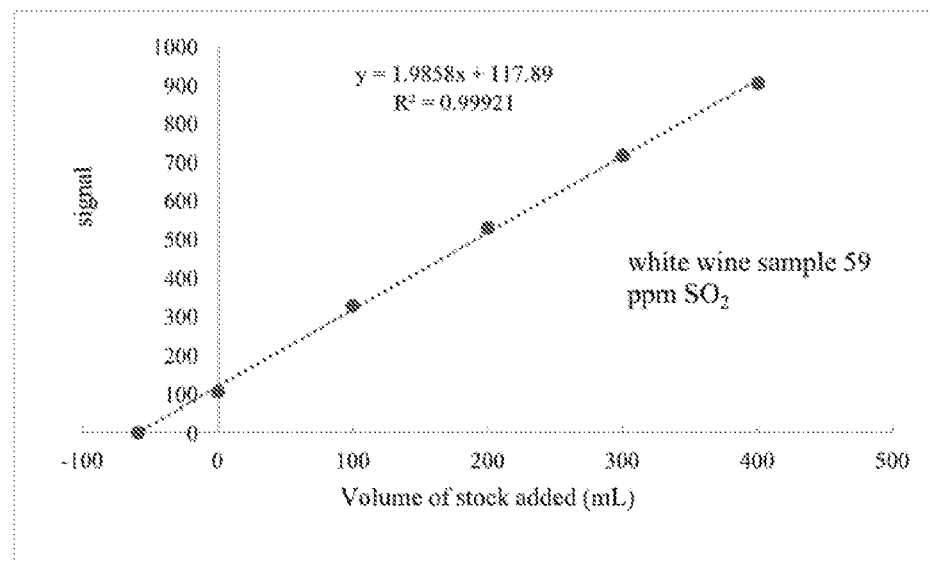
FIGS. 7(a) and 7(b) show the calibration curves for different concentrations of sulphur dioxide added to white wine and red wine respectively.
Figure 7:
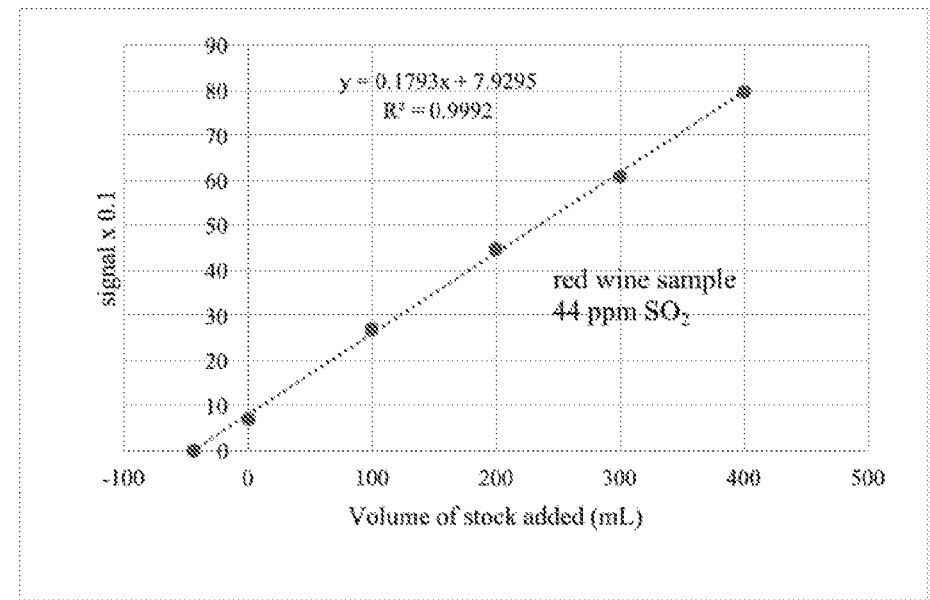

FIGS. 7(a) and 7(b) shows the results for the determination of $SO_2$ in, respectively, white and red wine. Using the standard addition methodology, the sample was spiked with progressively larger volumes of a standard $SO_2$ solution of known concentration. The results show that 1) the method works effectively in real samples of wine and 2) the method works in red or white wine. This contrasts with many of the common spectrophotometric methods for $SO_2$ analysis.

Figure 8:
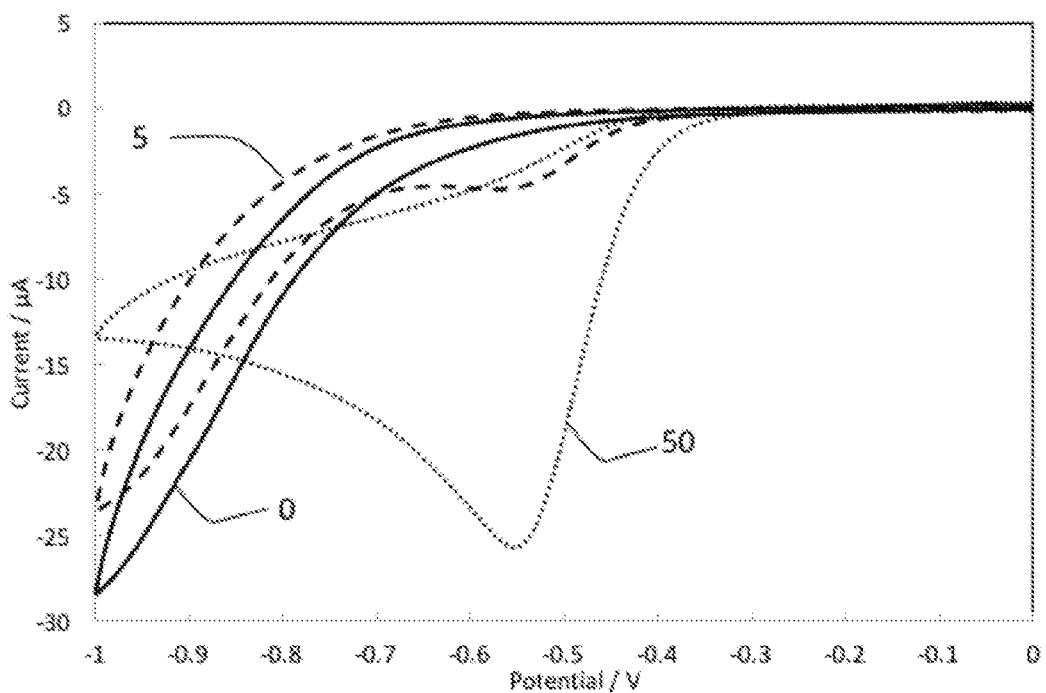
FIGS. 8(a) and 8(b) show cyclic voltammograms of different concentrations of $SO_2$ using particulate carbon and glassy carbon electrodes respectively.
Figure 8:
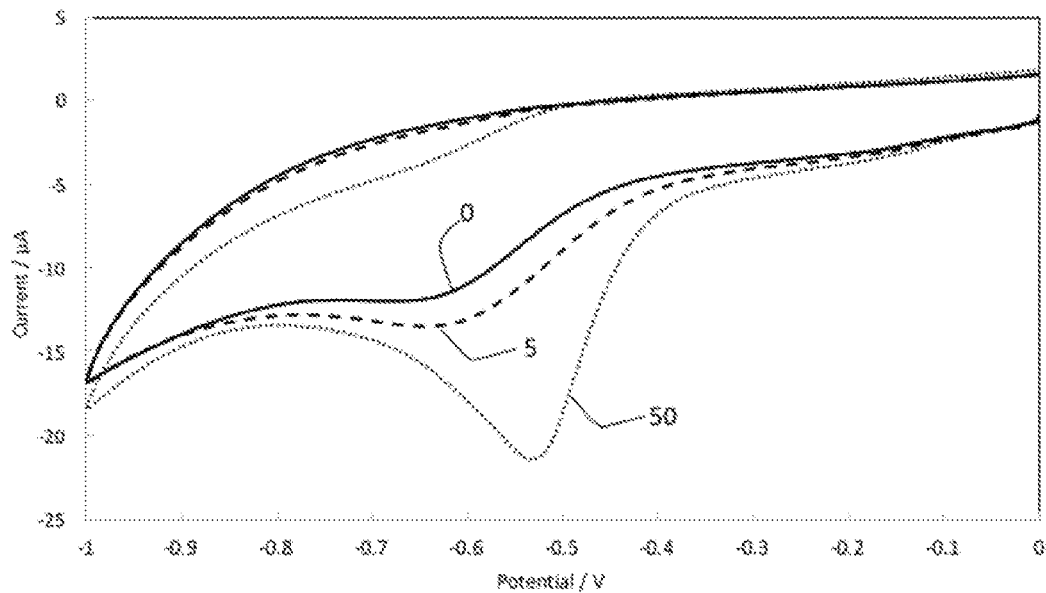

FIG. 8(a) shows the use of cyclic voltammetry (or linear scan voltammetry) for the detection of $SO_2$ using a printed particulate carbon electrode and a potentiostat. No reduction peak for dioxygen is observed in the sample with 0 ppm $SO_2$ (solid line).

FIG. 8(b) demonstrates the difficulty of using of cyclic voltammetry (or linear scan voltammetry) for the detection of $SO_2$ using a glassy carbon electrode and a potentiostat. A significant reduction peak for dioxygen is observed (solid line).

Figure 9:
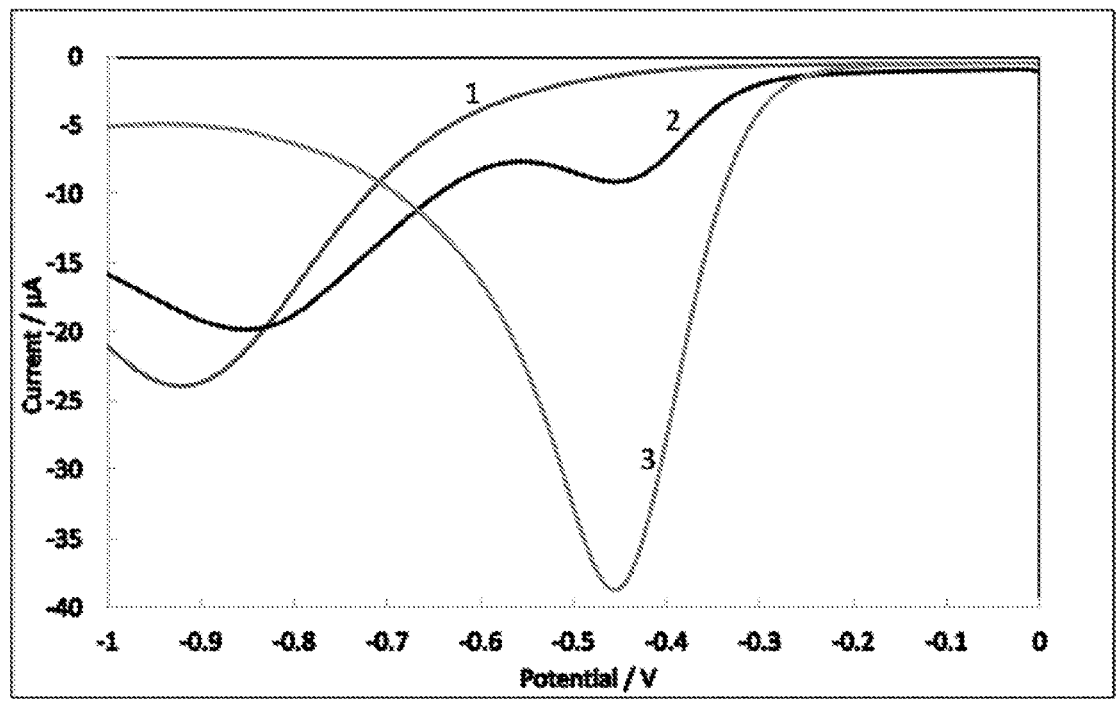
FIGS. 9(a) and 9(b) show square wave voltammograms of different concentrations of $SO_2$ using particulate carbon and glassy carbon electrodes respectively.
Figure 9:
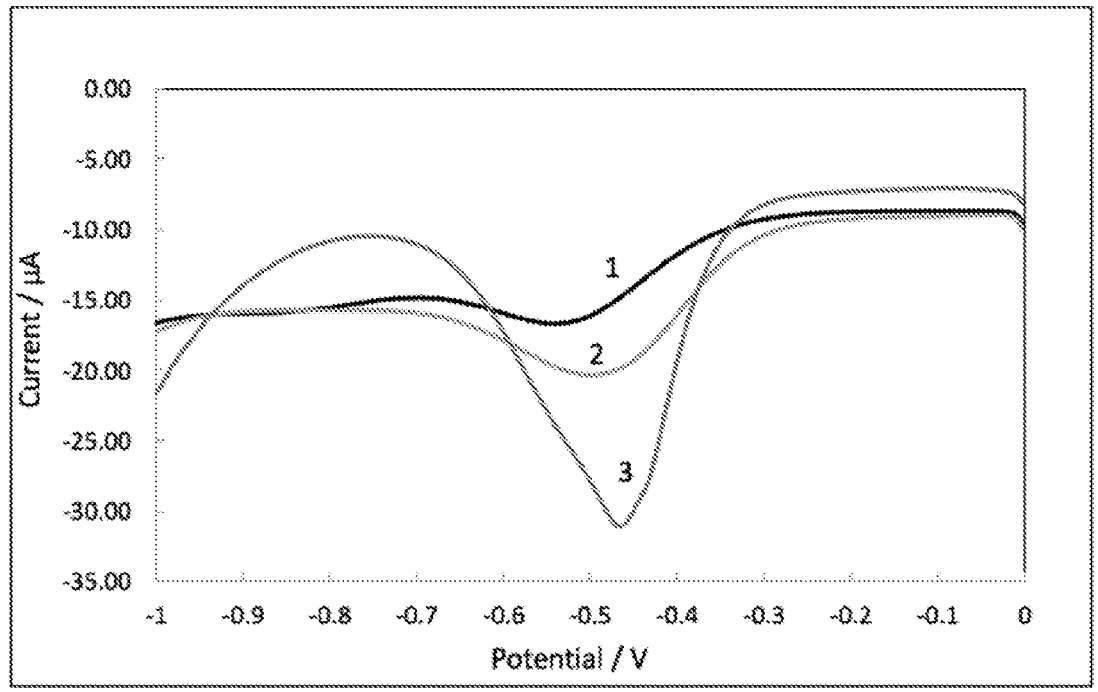

FIG. 9(a) shows the use of square wave voltammetry (or any pulsed technique) for the detection of $SO_2$ using a printed particulate carbon electrode and a potentiostat. No reduction peak for dioxygen is observed in the sample with 0 ppm $SO_2$ (plot 1). Sample 2 contains 5 ppm and sample 3 contains 50 ppm $SO_2$.

FIG. 9(b) demonstrates the difficulty of using square wave voltammetry (or any pulsed technique) for the detection of $SO_2$ using a glassy carbon electrode and a potentiostat. A significant reduction peak for dioxygen is observed (plot 1). Sample 2 contains 5 ppm and sample 3 contains 50 ppm $SO_2$.

In another illustrative embodiment, the presently disclosed methods may be performed by locating a printed sensor, said sensor comprising at least a particulate carbon working electrode and a counter electrode, in the head-space of a solution of an analyte which has a pH of about 1.8. This may be effected using 0.2M KCl/HCl or other acid/electrolyte solution.

This methodology addresses the problem of interference from polyphenols and other compounds in electrochemical analysis of wine. This involves acidification of the sample of wine in a sealed vial, so that gaseous $SO_2$ is released from the wine into the head-space above the liquid sample. An electrochemical sensor is positioned in the head-space above the liquid sample. The electrochemical sensor, (which may be a 2-electrode system or a 3-electrode system), is preferably a printed sensor with the working electrode composed of particulate carbon or copper or both. The electrodes are in contact with a thin membrane which is saturated in electrolyte solution. The $SO_2$ in the sample head-space diffuses into this thin layer of electrolyte solution, facilitating detection of $SO_2$ in the membrane without interference from polyphenols. The membrane may comprise any material which will hold a thin layer of liquid in intimate contact with the electrodes, while allowing gaseous $SO_2$ to diffuse into it. Fine nylon mesh may be used for the membrane as can paper. If paper is used, the sensor may be conveniently filled by capillary action using a paper-fluidic element.

Figure 10:
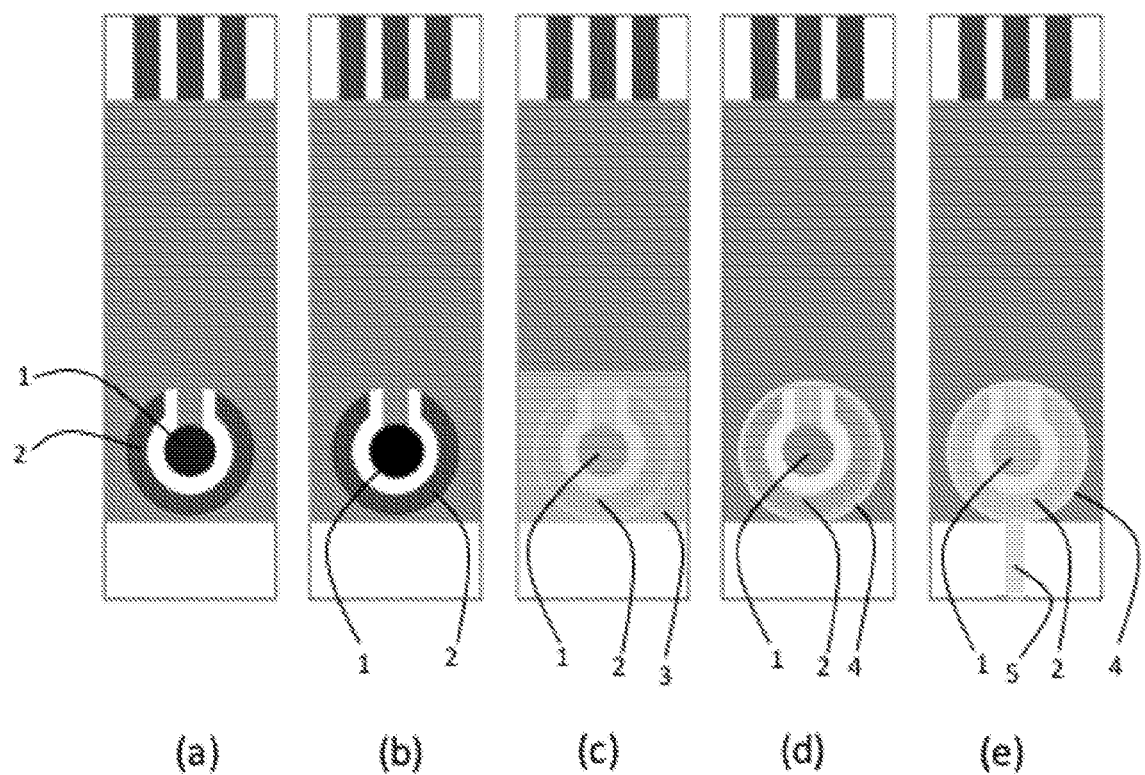
FIGS. 10(a) to 10(e) show schematic drawings of various electrodes according to embodiments of the present disclosure.

Illustrative experiments were performed with a custom-made electrode (Metrohm DropSens). FIG. 10 illustrates several, (a) to (e), custom designed screen printed electrodes consisting of, in each case, a counter electrode (2) made of silver/silver chloride, and a working electrode (1) made of particulate carbon (a) or copper (b).

FIG. 10 (c) illustrates the placement of a rectangular nylon mesh membrane (3) over the face of the electrodes, which in use is wetted with a solution of electrolyte.

FIG. 10(d) illustrates the placement of a paper membrane disc (4) comprising electrolyte solution over the face of the electrodes.

FIG. 10(e) illustrates the placement of a paper membrane disc (4) comprising electrolyte solution over the face of the electrodes. The disc includes wick (5) which facilitates wetting of the membrane. Before use, the wick is dipped in a solution of electrolyte.

Figure 11:
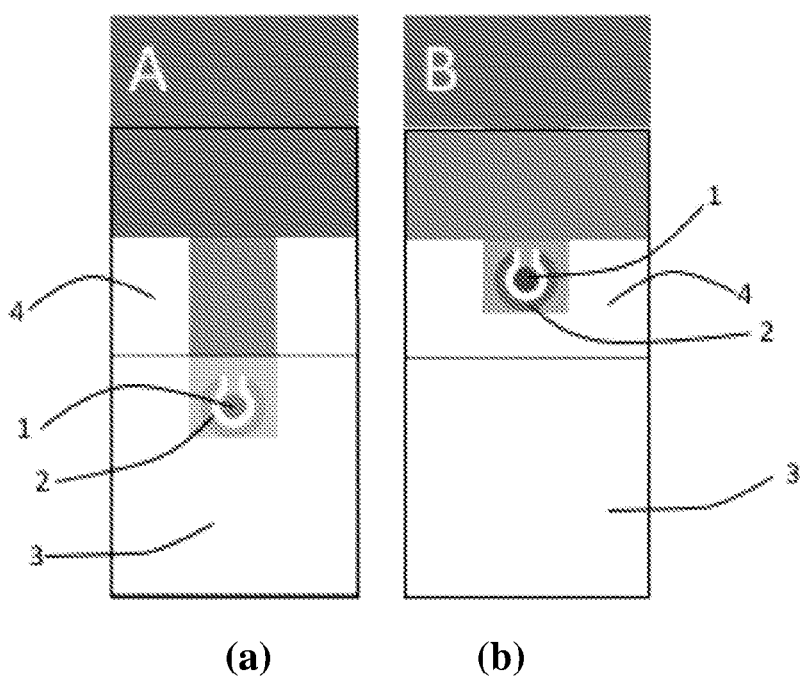
FIGS. 11(a) and 11(b) are schematic drawings of two modes of measurement according to embodiments of the present disclosure.

FIG. 11(a) depicts the "immersed" mode (also shown in FIG. 3), which is suitable for use with samples such as white wine, which do not contain significant concentrations of polyphenol. The electrode, comprising working electrode (1) and counter electrode (2) is immersed in a solution (3) of an analyte. Head space (4) above the solution is also illustrated.

FIG. 11(b) depicts the non-immersed or "head-space" mode, which is suitable for samples, such as red wine, which contain significant concentrations of polyphenol. The electrode, comprising working electrode (1) and counter electrode (2) is positioned in the head space (4) above solution of the analyte (3).

The head-space mode may also be used for samples such as white wine, which do not contain significant concentrations of polyphenol.

Discrimination against polyphenols is key to reductive determination of $SO_2$ in red wines, many of which contain these interfering components in high concentration. Surprisingly, rapid, accurate determination of sulphur dioxide was achieved when a working electrode comprising particulate carbon or copper contacted with a membrane comprising electrolyte solution was placed in the head-space above the solution comprising the analyte.

Figure 12:
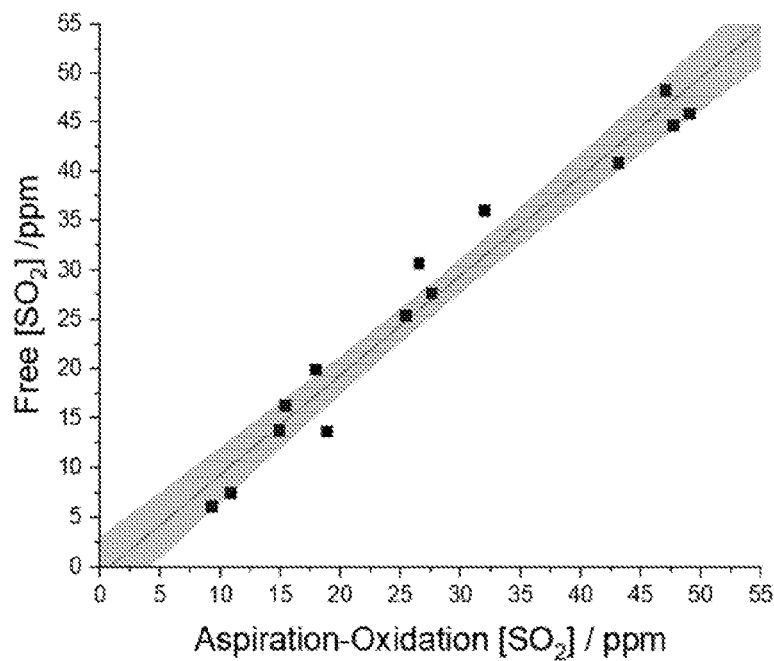
FIG. 12 shows the correlation with 95% confidence band, between free $SO_2$ concentration measured using a particulate carbon electrode (immersed mode) and free $SO_2$ concentration measured using standard aspiration-oxidation method, for fourteen white wine samples.

FIG. 12 illustrates the correlation between particulate carbon screen printed electrode measurements and aspiration-oxidation free sulphur dioxide results for fourteen white wines, with 95% confidence band. The working electrode measured the sulphur dioxide by immersion into acidified wine. The results indicate that across a wide range of free sulphur dioxide concentrations the present method correlates well with a standard method of measuring free sulphur dioxide present in white wine.

Figure 13:
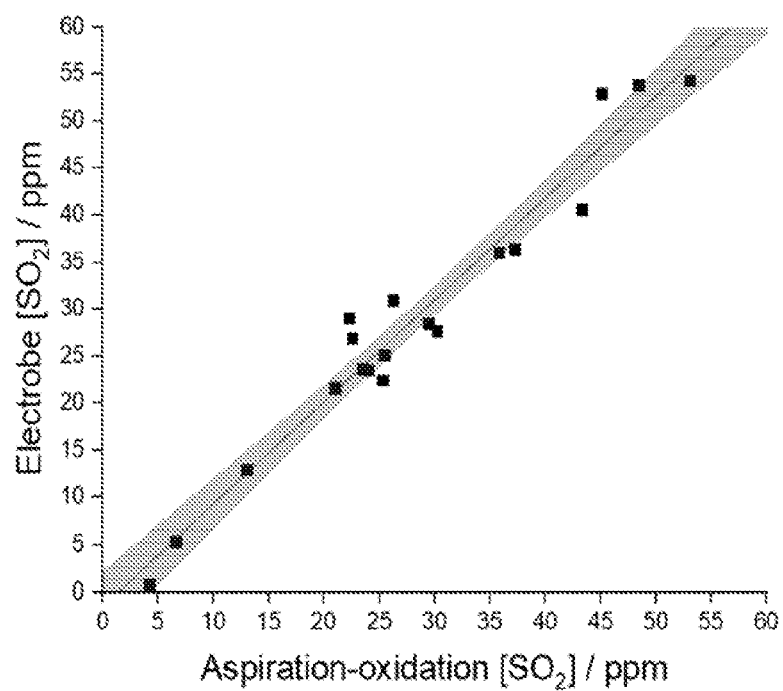
FIG. 13 shows the correlation, with 95% confidence band, between free $SO_2$ concentration measured using a particulate carbon electrode (non-immersed or head-space mode) and free $SO_2$ concentration measured using standard aspiration-oxidation method, for twenty red wine samples.

FIG. 13 illustrates the correlation between particulate carbon screen printed electrode measurements and aspiration-oxidation free sulphur dioxide results for 20 red wines, with 95% confidence band. The working electrode measured the sulphur dioxide in the head-space above the acidified wine. The results indicate that across a wide range of free sulphur dioxide concentrations the present method correlates well with a standard method of measuring free sulphur dioxide present in red wine.

Figure 14:
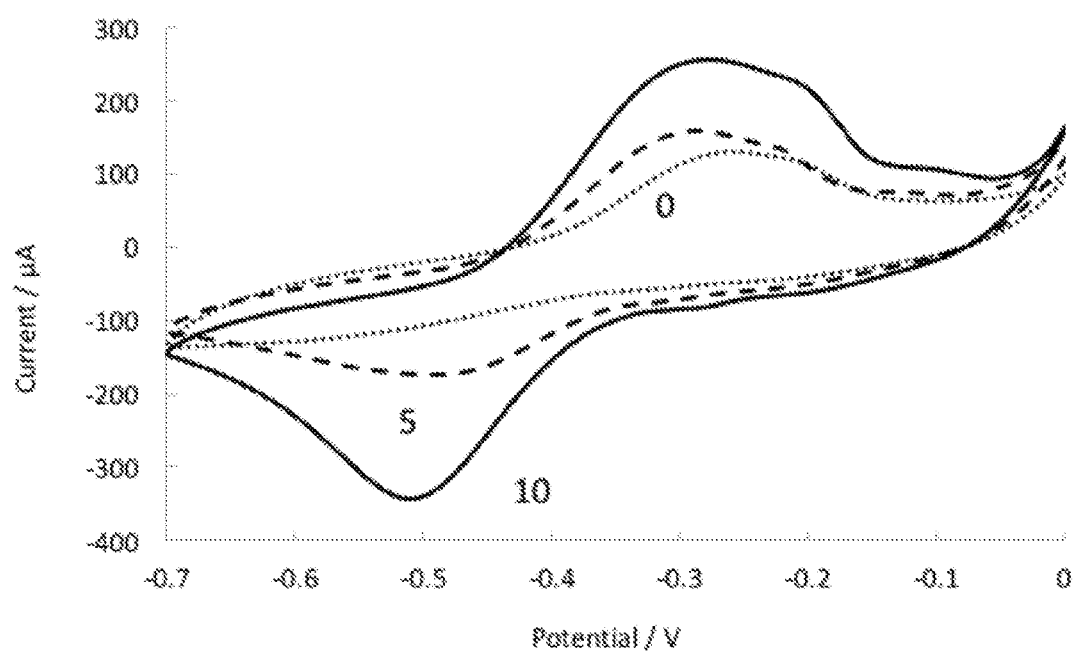
FIG. 14 shows cyclic voltammograms of different concentrations of $SO_2$ using a copper electrode in non-immersed (head space) mode.

FIG. 14 illustrates the use of cyclic voltammetry (or linear scan voltammetry) for the detection of $SO_2$ using a copper electrode in head space mode and a potentiostat. The dotted, dashed and solid lines represent 0, 5 and 10 ppm of $SO_2$ respectively.

It is evident that less than 5 ppm $SO_2$ is detectable with this system. As $SO_2$ electrochemistry is reversible at the copper electrode this leads to an enhanced signal when AC voltammetric or pulsed voltammetric techniques are used. Furthermore, as dioxygen reduction is irreversible, there is an enhanced discrimination against dioxygen when AC voltammetric or pulsed voltammetric techniques are used.

In one embodiment, there is provided a method for detecting or measuring the concentration of free sulphur dioxide via electrochemical reduction, said method comprising:
- (a) introducing into a solution comprising free sulphur dioxide a working electrode and a counter electrode, said working electrode having an active surface comprising one or both of particulate carbon and copper;
- (b) applying a time-variable voltammetric driving potential between the working and counter electrodes; and
- (c) measuring the resulting voltammetric response waveform.

The solution may comprise between about 1 and about 100 ppm dioxygen.

In another embodiment, there is provided a method for detecting or measuring the concentration of free sulphur dioxide via electrochemical reduction, said method comprising:
- (a) introducing into a solution comprising free sulphur dioxide a working electrode and a counter electrode, wherein the working electrode does not produce a voltammetric response due to the reduction of dioxygen which significantly overlaps with a voltammetric response due to the reduction of sulphur dioxide;
- (b) applying a time-variable voltammetric driving potential between the working and counter electrodes; and
- (c) measuring the resulting voltammetric response waveform.

The solution may comprise between about 1 and about 100 ppm dioxygen.

In another embodiment, there is provided a method for detecting or measuring the concentration of free sulphur dioxide in wine via electrochemical reduction, said method comprising:
- (a) introducing into wine a working electrode and a counter electrode, said working electrode having an active surface comprising one or more of particulate carbon and copper;
- (b) applying a time-variable voltammetric driving potential between the working and counter electrodes; and
- (c) measuring the resulting voltammetric response waveform.

The wine may comprise between about 1 and about 100 ppm dioxygen.

In another embodiment, there is provided a method for detecting or measuring the concentration of free sulphur dioxide in wine via electrochemical reduction, said method comprising:
- (a) introducing into wine a working electrode and a counter electrode, wherein the working electrode does not produce a voltammetric response due to the reduction of dioxygen which significantly overlaps with a voltammetric response due to the reduction of sulphur dioxide;
- (b) applying a time-variable voltammetric driving potential between the working and counter electrodes; and
- (c) measuring the resulting voltammetric response waveform.

The wine may comprise between about 1 and about 100 ppm dioxygen.

In another embodiment, there is provided a method for detecting or measuring the concentration of free sulphur dioxide via electrochemical reduction, said method comprising:
- (a) introducing into a head-space adjacent to a solution comprising free sulphur dioxide a working electrode and a counter electrode, said working electrode having an active surface comprising one or both of particulate carbon and copper, said working electrode and counter electrode being in contact with a membrane, said membrane comprising electrolyte solution;
- (b) applying a time-variable voltammetric driving potential between the working and counter electrodes; and
- (c) measuring the resulting voltammetric response waveform.

The solution may comprise between about 1 and about 100 ppm dioxygen.

In another embodiment, there is provided a method for detecting or measuring the concentration of free sulphur dioxide via electrochemical reduction, said method comprising:
- (a) introducing into a head-space adjacent to a solution comprising free sulphur dioxide a working electrode and a counter electrode, wherein the working electrode does not produce a voltammetric response due to the reduction of dioxygen which significantly overlaps with a voltammetric response due to the reduction of sulphur dioxide, said working electrode and counter electrode being in contact with a membrane, said membrane comprising electrolyte solution;

(b) applying a time-variable voltammetric driving potential between the working and counter electrodes; and (c) measuring the resulting voltammetric response waveform.

The solution may comprise between about 1 and about 100 ppm dioxygen.

In another embodiment, there is provided a method for detecting or measuring the concentration of free sulphur dioxide in wine via electrochemical reduction, said method comprising:

(a) introducing into a head-space adjacent to wine comprising free sulphur dioxide a working electrode and a counter electrode, said working electrode having an active surface comprising one or both of particulate carbon and copper, said working electrode and counter electrode being in contact with a membrane, said membrane comprising electrolyte solution;

(b) applying a time-variable voltammetric driving potential between the working and counter electrodes; and (c) measuring the resulting voltammetric response waveform.

The wine may comprise between about 1 and about 100 ppm dioxygen.

In another embodiment, there is provided a method for detecting or measuring the concentration of free sulphur dioxide in wine via electrochemical reduction, said method comprising:

(a) introducing into a head-space adjacent to wine comprising free sulphur dioxide a working electrode and a counter electrode, wherein the working electrode does not produce a voltammetric response due to the reduction of dioxygen which significantly overlaps with a voltammetric response due to the reduction of the sulphur dioxide, said working electrode and counter electrode being in contact with a membrane, said membrane comprising electrolyte solution;

(b) applying a time-variable voltammetric driving potential between the working and counter electrodes; and (c) measuring the resulting voltammetric response waveform.

The wine may comprise between about 1 and about 100 ppm dioxygen.

In any one of the herein disclosed embodiments, the magnitude of the voltammetric response due to the reduction of dioxygen, at the potential of the peak voltammetric response due to the reduction of analyte, is less than 20%, or less than 10%, or less than 5%, or less than 2%, or less than 1% of the response due to reduction of analyte, when said analyte is present at a concentration of 5 ppm.

Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A system for detecting or measuring a concentration of an analyte via electrochemical reduction, said system comprising:

(a) a source of time-variable voltammetric driving potential;

(b) a working electrode, said working electrode having an active surface comprising one or both particulate carbon and copper;

(c) a counter electrode; and (d) a means to measure a voltammetric response waveform;

wherein the working electrode and the counter electrode are connected to the source of time-variable voltammetric driving potential; and wherein the analyte is free sulphur dioxide.

2. A system according to claim 1, further comprising a voltammetric cell, said cell comprising a solution comprising the analyte.

3. A system according to claim 2, wherein one of the following applies:

i) the working electrode and counter electrode are immersed in the solution comprising the analyte; or ii) the working electrode and the counter electrode are in contact with a membrane comprising electrolyte solution.

4. A system according to claim 3, part ii, wherein the working electrode, counter electrode and contacted membrane comprising electrolyte solution are located in a head-space of the voltametric cell.

5. A system according to claim 2, wherein one or more of the following applies:

i) the solution comprising the analyte has a pH between about 0.5 and about 5, or between about 0.6 and about 4, or between about 0.6 and about 3, or between about 0.6 and about 2;

ii) a reduction potential of the analyte is between about +0.2 volts and about −0.7 volts;

iii) the solution comprising the analyte comprises less than about 100 ppm dioxygen, or less than about 50 ppm, or less than about 30 ppm, or less than about 20 ppm, or less than about 10 ppm, or less than about 5 ppm dioxygen;

iv) the solution comprising the analyte comprises between about 1 and about 100 ppm dioxygen, or between about 1 ppm and about 50 ppm dioxygen, or between about 0.5 ppm and about 30 ppm dioxygen, or between about 0.5 ppm and about 20 ppm dioxygen, or between about 0.5 ppm and about 10 ppm dioxygen, or between about 0.5 ppm and about 5 ppm dioxygen; and v) the solution comprising the analyte is a liquid food product.

6. A system according to claim 5, wherein the liquid food product is a beverage.

7. A system according to claim 6, wherein the beverage is selected from the group consisting of wine and beer.

8. A system according to claim 7, wherein the wine comprises from about 0.1 g/L to about 4 g/L polyphenols.

9. A system according to claim 3, part ii, wherein one or more of the following applies:

i) the membrane has a thickness from about 0.01 micron to about 1000 micron, or from about 0.1 micron to about 500 micron, or from about 1 micron to about 200 micron, or from about 10 micron to about 100 micron;

ii) the membrane is a hydrophilic microporous membrane; and iii) the membrane comprises nylon or paper.

10. A system according to claim 1, wherein one of the following applies:
   i) the source of time variable voltammetric driving potential and the means to measure the voltammetric response waveform comprise a potentiostat, said potentiostat being connected to the working electrode and counter electrode; or
   ii) the source of time variable voltammetric driving potential and the means to measure the voltammetric response waveform comprise a mobile computing device, said mobile computing device being connected to the working electrode and counter electrode.

11. A system according to claim 10, part ii, wherein one or both of the following applies:
   i) the working electrode and the counter electrode are wirelessly connected to the mobile computing device; and
   ii) wherein the mobile computing device is a mobile phone.

12. A system according to claim 1, wherein one or more of the following applies:
   i) the working electrode does not produce the voltammetric response waveform due to a reduction of dioxygen which significantly overlaps with the voltammetric response waveform due to a reduction of the analyte;
   ii) a magnitude of the voltammetric response waveform due to a reduction of dioxygen, at a potential of a peak voltammetric response waveform response due to a reduction of the analyte is less than 20%, or less than 10%, or less than 5%, or less than 2%, or less than 1% or a response due to a reduction of the analyte when said analyte is present at a concentration of 5 ppm;
   iii) the working electrode does not substantially electrochemically reduce dioxygen at a potential between about 0 and about −1.0 volts;
   iv) the working electrode is a screen printed particulate carbon electrode, a graphene coated electrode, or a copper electrode;
   v) the time-variable voltammetric driving potential is selected from a DC ramp, a series of square wave pulses superimposed on a DC ramp or an AC waveform superimposed on a DC ramp; and
   vi) the system further comprises a reference electrode.

13. A system according to claim 12, part v, wherein the time-variable voltammetric driving potential is selected from a series of square wave pulses superimposed on the DC ramp or the AC waveform superimposed on the DC ramp.

14. A system according to claim 12, part v, wherein one or more of the following applies:
   i) a frequency of the AC or square wave pulse component is between about 10 Hz and about 200 Hz;
   ii) an amplitude of the AC or square wave pulse component is between about 5 mV and about 400 mV;
   iii) the ramp has a DC scan rate of an order of about 100 mV/s; and
   iv) the potential is scanned from any value between more positive than about −0.3 V to about −1.0 V.

15. A system according to claim 1, wherein the free sulphur dioxide is present in an amount between about 1 ppm and about 50 ppm and the dioxygen is present in an amount between about 1 ppm and about 50 ppm.

16. A method for detecting or measuring a concentration of an analyte via electrochemical reduction, said method comprising:
   (a) either,
      (i) introducing into a solution comprising the analyte a working electrode and a counter electrode; or
      (ii) introducing into a head-space adjacent to a solution comprising the analyte a working electrode and a counter electrode, said working electrode and counter electrode being in contact with a membrane, said membrane comprising an electrolyte solution;
      wherein both (i) and (ii) said working electrode has an active surface comprising one or both of particulate carbon and copper;
   (b) applying a time-variable voltammetric driving potential between the working and counter electrodes; and
   (c) measuring a resulting voltammetric response waveform; and
   wherein the analyte is free sulphur dioxide.

17. A method according to claim 16, wherein one of the following applies:
   i) the time-variable voltammetric driving potential and the resulting voltammetric response waveform are respectively applied and measured via a potentiostat; or
   ii) the time-variable voltammetric driving potential and the resulting voltammetric response waveform are respectively applied and measured via a mobile computing device.

18. A method according to claim 17, wherein one or both of the following applies:
   i) the application and measuring are performed wirelessly; and
   ii) the mobile computing device is a mobile phone.

19. A method according to claim 16, wherein one or more of the following applies:
   i) the working electrode does not produce the resulting voltammetric response waveform due to a reduction of dioxygen which overlaps with the voltammetric response waveform due to a reduction of the analyte;
   ii) a magnitude of the voltammetric response waveform due to a reduction of dioxygen, at a potential of a peak voltammetric response due to a reduction of the analyte is less than 20%, or less than 10%, or less than 5%, or less than 2%, or less than 1% or a response due to a reduction of the analyte, when said analyte is present at a concentration of 5 ppm;
   iii) the working electrode does not substantially electrochemically reduce dioxygen at a potential between about 0 volts and about −1.0 volts;
   iv) the working electrode is a screen printed particulate carbon electrode, a graphene coated electrode, or copper electrode;
   v) the time-variable voltammetric driving potential is selected from a DC ramp, a series of square wave pulses superimposed on the DC ramp, or an AC waveform superimposed on the DC ramp; and
   vi) the system further comprises a reference electrode.

20. A method according to claim 19, part v, wherein the time-variable voltammetric driving potential is selected from the series of square wave pulses superimposed on the DC ramp or the AC waveform superimposed on the DC ramp.

21. A method according to claim 19, part v, wherein one or more of the following applies:
   i) a frequency of the AC or square wave pule component is between about 10 Hz and about 200 Hz;
   ii) an amplitude of the AC or square wave pulse component is between about 5 mV and about 400 mV;
   iii) the ramp has a DC scan rate of an order of about 100 mVs; and
   iv) the potential is scanned from any value between more positive than about −0.3 V to about −1.0 V.

22. A method according to claim 16, wherein one or more of the following applies:
  i) the solution comprising the analyte has a pH between about 0.5 and about 5, or between about 0.6 and about 4, or between about 0.6 and about 3, or between about 0.6 and about 2;
  ii) a reduction potential of the analyte is between about +0.2 volts and about −0.7 volts;
  iii) the solution comprising the analyte comprises less than about 100 ppm dioxygen, or less than about 50 ppm, or less than about 30 ppm, or less than about 20 ppm, or less than about 10 ppm, or less than about 5 ppm dioxygen;
  iv) the solution comprising the analyte comprises between about 1 ppm and about 100 ppm dioxygen, or between about 1 ppm and about 50 ppm dioxygen, or between about 0.5 ppm and about 30 ppm dioxygen, or between about 0.5 ppm and about 20 ppm dioxygen, or between about 0.5 ppm and about 10 ppm dioxygen, or between about 0.5 ppm and about 5 ppm dioxygen; and
  v) the solution comprising the analyte is a liquid food product.

23. A method according to claim 22, wherein the liquid food product is a beverage.

24. A method according to claim 23, wherein the beverage is selected from the group consisting of wine and beer.

25. A method according to claim 24, wherein the wine comprises from about 0.1 g/L to about 4 g/L polyphenols.

26. A method according to claim 16, wherein the free sulphur dioxide is present in an amount between about 1 ppm and about 50 ppm and the dioxygen is present in an amount between about 1 ppm and about 50 ppm.

27. A method according to claim 16, wherein one or more of the following applies:
  i) the membrane has a thickness from about 0.01 micron to about 1000 micron, or from about 0.1 micron to about 500 micron, or from about 1 micron to about 200 micron, or from about 10 micron to about 100 micron;
  ii) the membrane is a hydrophilic microporous membrane; and
  iii) the membrane comprises nylon or paper.

* * * * *